United States Patent [19]

Aberkane et al.

[11] Patent Number: 5,284,592
[45] Date of Patent: Feb. 8, 1994

[54] (POLY) SULFURIZED CARBOXYLIC COMPOUNDS, THEIR PREPARATION AND THEIR USE AS PETROLEUM ADDITIVES FOR LUBRICATING OILS

[75] Inventors: Ourida Aberkane, Fameck; Maurice Born, Nanterre; Jean-Luc Mieloszynski, Montigny les Metz; Daniel Paquer, Vandoeuvre; Guy Parc, Rueil Malmaison, all of France

[73] Assignee: Institut Francais Du Petrole, Rueil Malmaison, France

[21] Appl. No.: 872,196

[22] Filed: Apr. 22, 1992

[30] Foreign Application Priority Data

Apr. 23, 1991 [FR] France .................... 91 05091

[51] Int. Cl.$^5$ ........................................... C10M 135/26
[52] U.S. Cl. ............................. 252/48.006; 560/195
[58] Field of Search ..................... 252/48.6; 560/195

[56] References Cited

U.S. PATENT DOCUMENTS

| | | | |
|---|---|---|---|
| 2,743,293 | 4/1956 | DeGroote . | |
| 4,335,004 | 6/1982 | Efner | 252/48.6 |
| 4,612,131 | 9/1986 | Rosenberger | 252/48.6 |
| 4,661,272 | 4/1987 | Marquis et al. | 252/48.6 |
| 4,699,939 | 10/1987 | Orban et al. | 252/48.6 |
| 4,902,438 | 2/1990 | O'Connor | 252/48.6 |

FOREIGN PATENT DOCUMENTS 955089  4/1964  United Kingdom .
960184  6/1964  United Kingdom .

OTHER PUBLICATIONS

"Resume", 606,732, English abstract of Be-A-606,732.

Primary Examiner—Jacqueline V. Howard
Attorney, Agent, or Firm—Millen, White, Zelano & Branigan

[57] ABSTRACT

Novel (poly)sulfurized carboxylic compounds, their preparation, and their use as additives to lubricating oils are disclosed. Such novel carboxylic compounds are more particularly esters of the general formula:

$$[R^3-OC(O)-]_q R^2 \{-C(O)O-(CH_2)_m-CH_{3-z}-[-(CH_2)_n-S_x-R^1]_z\}_p \quad (1)$$

wherein $R^1$ is a saturated or unsaturated monovalent aliphatic radical with 1 to 30 carbon atoms; the number x is equal to or greater than 1; z equals 1 or 2; when z equals 1, n is an integer from 0 to 5 and m an integer from 0 to 0.5, with m+n an integer from 1 to 10; when z equals 2, n is an integer from 1 to 5 and m an integer from 0 to 5, with m+n an integer from 1 to 10; $R^2$ is a hydrocarbon radical with 1 to 31 carbon atoms and a valency of p+q; $R^3$ is a hydrogen atom or an aliphatic radical with 1 to 30 carbon atoms; p is an integer from 1 to 4; and q is an integer from 0 to 3, with p+q being an integer from 1 to 4. They are obtained by esterifying carboxylic acid $R^2(-COOH)_{p+q}$ with a (poly)sulfurized monoalcohol:

$$[R^1-S_x-(CH_2)_n-]_z CH_{3-z}-(CH_2)_m-OH$$

and possibly an alcohol $R^3OH$. They are used as anti-wear and extreme pressure additives in lubricating oils.

22 Claims, No Drawings

(POLY) SULFURIZED CARBOXYLIC COMPOUNDS, THEIR PREPARATION AND THEIR USE AS PETROLEUM ADDITIVES FOR LUBRICATING OILS

SUMMARY OF THE INVENTION

The invention concerns new (poly)sulphurised carboxylic compounds, acids and esters, their preparation and their use as petroleum additives, particularly as anti-wear and extreme pressure additives for lubricating oils.

Anti-wear and extreme pressure additives have been used for several decades, particularly in engine oils, transmission fluids and hydraulic fluids. Many types of additives have thus been developed, and several of them have very substantially reduced deterioration and consequently extended the life of the mechanisms involved.

Of the many anti-wear and extreme pressure additives which have been studied, dialkyl and diaryldithiophosphates and metallic (particularly zinc) dialkyldithiocarbamates, alkylthiophosphates, tricresylphosphate, didodecylphosphate, sulphurised terpenes, sulphurous spermaceti oil and many chlorinated compounds have proved to be the most active and have seen considerable industrial development. Some of them are described in patents U.S. Pat. Nos. 2,364,283, 2,364,284, 2,365,938, 2,410,650, 2,438,876 and 3,190,833. They are generally compounds containing heteroatoms such as sulphur and phosphorus, either alone (e.g. tricresylphosphate, sulphurised terpenes or dithiocarbamates), or in association (e.g. metallic dialkyldithiophosphates or alkylthiophosphates).

Some of the sulphurous compounds may contain chemical functions which give the compound physics-chemical properties or improve its mechanical performance in its application as an additive. These include phenol, nitrile, sulphoxide, xanthate functions and the like. American patents U.S. Pat. Nos. 3,434,852, 3,984,336 and 3,994,923 may be cited in this connection.

The quantity of sulphur contained in the molecule of these sulphurous compounds is generally established by the stoichiometry of the reactions involved in their synthesis. The compounds consequently have anti-wear and extreme pressure properties which cannot be modified.

New sulphurous compounds which can be used as additives for lubricants have now been discovered, where the proportion of sulphur contained in the molecule can be modified. Their anti-wear and extreme pressure properties can therefore be changed at will.

The compounds of the invention are defined as being (poly)sulphurised. This means that they may contain in their molecule either one or more isolated sulphur atoms (monosulphurised compounds) or one or more chains of a plurality of sulphur atoms (polysulphurised compounds).

The (poly)sulphurised carboxylic compounds of the invention may be defined generally by the fact that they are of the following formula

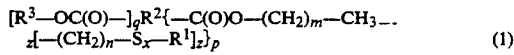  (1)

wherein $R^1$ represents a saturated or unsaturated monovalent aliphatic radical with 1 to 30, preferably 1 to 12 carbon atoms; x is a number equal to or greater than 1; z equals 1 or 2; when z equals 1, n is an integer from 0 to 5 and m an integer from 0 to 5, with m+n an integer from 1 to 10; when z equals 2, n is an integer from 1 to 5 and m an integer from 0 to 5, with m+n an integer from 1 to 10; $R^2$ is a hydrocarbon radical with 1 to 51 carbon atoms and a valency of p+q; $R^3$ is a hydrogen atom or a monovalent aliphatic radical with 1 to 30 carbon atoms; p is an integer from 1 to 4; and q is an integer from 0 to 3, with p+q being an integer from 1 to 4.

These compounds thus comprise esters formed by a mono or polycarboxylic acid of the formula $R^2[C(O)OH]_{p+q}$ (2) and a (poly)sulphurised monoalcohol of the general formula:

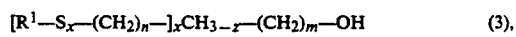  (3), possibly with an aliphatic monoalcohol $R^3OH$ (4), where $R^1$, $R^2$, $R^3$, x, z, n, m, p and q have the same meanings as before; at least one of the carboxylic functions of the formula (2) acid being esterified by a formula (3) (poly)sulphurised alcohol.

Carboxylic compounds comprising esters of monocarboxylic acids, or esters of polycarboxylic (di, tri or tetracarboxylic) acids where all the carboxylic functions are esterified by a (poly)sulphurised monoalcohol of formula (3) are considered more particularly in the invention. These esters thus correspond to formula (1) in which q equals zero.

The formula (2) carboxylic acids may be selected from aliphatic mono or polycarboxylic acids with 2 to 54 carbon atoms or cycloaliphatic or aromatic ones with 6 to 20 carbon atoms. They may more particularly be mono, di, tri or tetracarboxylic acids.

Some examples of such acids are:
saturated aliphatic monocarboxylic acids, such as acetic, propionic, butyric, caproic, caprylic, capric, palmitic or stearic acid;
unsaturated aliphatic monocarboxylic acids, such as acrylic, methacrylic, oleic, ricinoleic, linoleic, linolenic or erucic acid;
saturated or unsaturated aliphatic dicarboxylic acids, such as oxalic, malonic, succinic, maleic, adipic or azelaic acid or acids which are dimers of oleic, linoleic and/or linolenic acid;
saturated or unsaturated aliphatic tricarboxylic acids, such as acids which are trimers of oleic, linileic and-/or linolenic acid;
cycloaliphatic monocarboxylic acids, such as cyclohexane carboxylic acid;
cycloaliphatic dicarboxylic acids, such as cyclohexane dicarboxylic acid;
aromatic monocarboxylic acids, such as benzoic acid, toluic acids or salicylic acid;
aromatic dicarboxylic acids, such as orthophthalic or paraphthalic acid;
aromatic tricarboxylic acids, such as trimellitic or trimesitic acid;
and aromatic tetracarboxylic acids, such as pyromellitic acid, 4,4'-biphenyltetracarboxylic acid or 4,4'-diphenylethertetracarboxylic acid.

It is preferable in the invention for the carboxylic acid in question to be an aliphatic monocarboxylic acid with 2 to 22 carbon atoms. In formula (1) for the ester, q then equals zero, p equals 1 and $R^2$ is a monovalent aliphatic radical with 1 to 21 carbon atoms.

The above-mentioned (poly)sulphurised monoalcohols of formula (3) may more particularly be primary monoalcohols of the formula $R^1-S_x-(CH_2)_n-CH$-

$_2$OH (in cases where z=1 and m=0), or secondary monoalcohols of the formula: [R$^1$—S$_x$—(CH$_2$)$_n$—]$_2$.CHOH (in cases where z=2 and m=0).

In the above formulae the radical R$^1$ is preferably a saturated or unsaturated monovalent aliphatic radical with 1 to 12 carbon atoms; n is an integer from 1 to 5; and x is a number greater than or equal to 1.

Of the polysulphurised monoalcohols, i.e. those where x is greater than 1, according to the method by which they are prepared, we shall consider firstly so-called stoichiometric compounds, where the value of x is a whole value, e.g. 2, 3 or over: these will be primary monoalcohols which are disulphurised, trisulphurised etc; and secondary monoalcohols which are bis(disulphurised), bis(trisulphurised) etc. Secondly we shall consider so-called statistical products, comprising mixtures in varying proportions of compounds where x takes on a whole value (1, 2 or 3 etc), the value varying from one constituent of the mixture to another. The value of x given for the mixture is then a mean value which may or may not be whole. If it is close to 2, 3 etc we shall also speak in that case of disulphurised, trisulphurised primary monoalcohols etc and of bis (disulphurised), bis(trisulphurised) secondary monoalcohols etc.

Some examples of monoalcohols which may be used to form the (poly)sulphurised carboxylic compounds of the invention are:

monosulphurised primary monoalcohols such as t.Bu—S—(CH$_2$)$_2$—OH; t.Bu—S—(CH$_2$)$_3$—OH; t.Bu—S—(CH$_2$)$_6$—OH; methallyl —S—(CH$_2$)$_2$—OH; methyallyl-S—(CH$_2$)$_3$—OH; and methallyl-S—(CH$_2$)$_6$—OH;

bis(monosulphurised) secondary monoalcohols such as (t.Bu—S—CH$_2$—)$_2$CHOH;

disulphurised primary monoalcohols (stoichiometric or statistical), such as t.Bu—S$_2$—(CH$_2$)$_2$—OH; t.Bu—S$_2$—(CH$_2$)$_3$—OH; t.Bu—S$_2$—(CH$_2$)$_6$—OH; methallyl-S$_2$—(CH$_2$)$_2$—OH; methallyl-S$_2$—(CH$_2$)$_3$—OH; methallyl-S$_2$—(CH$_2$)$_4$—OH; methallyl-S$_2$—(CH$_2$)$_5$—OH; and methallyl-S$_2$—(CH$_2$)$_6$—OH;

bis(disulphurised) secondary monoalcohols such as (t.Bu—S$_2$—CH$_2$—)$_2$CHOH;

trisulphurised primary monoalcohols such as t.Bu—S$_3$—(CH$_2$)$_2$—OH; and the like.

The (poly)sulphurised monoalcohols considered above may be prepared by various methods.

Thus monosulphurised monoalcohols of the formula R$^1$—S—(CH$_2$)$_n$—CH$_2$OH, where R$^1$ represents a monovalent aliphatic radical containing e.g. from 1 to 12 carbon atoms, which may be saturated or unsaturated, such as the tertiobutyl radical or the methallyl radical, and where n is an integer e.g. from 1 to 5, may be obtained by reacting a thiol R$^1$SH with a chloroalcohol Cl—(CH$_2$)$_n$—CH$_2$—OH in an alkaline medium. Similarly, monosulphurised alcohols of the formula [R$^1$—S—(CH$_2$)$_n$]$_2$CH—OH are obtained by reacting a thiol R$^1$SH in an alkaline medium with a secondary chloro-alcohol [Cl(C$_2$)$_n$]$_2$CHOH.

Unsaturated monosulphurised monoalcohols such as methallyl-S—CH$_2$—CH$_2$OH may further be obtained by reacting alkenyl chloride (e.g. methallyl) with 2-mercaptoethanol SH—CH$_2$—CH$_2$—OH in an alkaline medium.

To prepare disulphurised monoalcohols of the formula R$^1$—S$_2$—CH$_2$—CH$_2$—OH, where R$^1$ represents a saturated or unsaturated monovalent aliphatic radical containing e.g. from 1 to 12 carbon atoms, such as the tertiobutyl or the methallyl radical, methoxycarbonylsulphenyl chloride CH$_3$—O—CO—S—Cl is reacted with 2-mercaptoethanol to form the disulphide CH$_3$—O—CO—S$_2$—CH$_2$—CH$_2$—OH, which is then reacted with the thiol R$^1$SH.

A general method of preparing polysulphurised monoalcohols of the formula R$^1$—S$_x$—(CH$_2$)$_n$—CH$_2$OH where R$^1$ is a saturated or unsaturated monovalent aliphatic radical containing e.g. from 1 to 12 carbon atoms, where n is an integer from 1 to 5 and where x is a number greater than 1, comprises (a) preparing a thiolate R$^1$—S$_x$—Na by reacting thiol R$^1$SH with caustic soda in an aqueous or alcoholic medium to form the thiolate R$^1$—S—Na, then by reacting that thiolate with an appropriate proportion of elemental sulphur, also in an aqueous or alcoholic medium; then (b) reacting the thiolate R$^1$—S$_x$—Na obtained with chloro-alcohol Cl—(CH$_2$)$_n$—CH$_2$OH.

The polysulphurised monoalcohol is obtained in the form of a mixture of compounds, for which the value of x given is a mean value (statistical compound).

Secondary polysulphurised monoalcohols (R$^1$—S$_x$—CH$_2$—)$_2$CHOH may be obtained by the same method, using secondary chloro-alcohol (Cl—CH$_2$—)$_2$CHOH.

By following this preparation method, when R$^1$ represents an unsaturated aliphatic radical such as methallyl, one generally obtains a minor proportion of symmetrical sulphides R$^1$—S$_x$—R$^1$ as well as the required polysulphurised monoalcohol. The symmetrical sulphides may either be removed, e.g. by separation on silica gel, or left in the product.

Another procedure for preparing disulphurised monoalcohols of the formula R$^1$—S$_x$—(CH$_2$)$_n$—CH$_2$OH, where R$^1$ is an unsaturated aliphatic radical such as methallyl, e.g. with n from 2 to 5, is to react thiolate R$^1$—S—Na with sodium hydroxyalkyl thiosulphate HO(CH$_2$)$_n$—CH$_2$—S$_2$O$_3$Na. The stoichiometric disulphurised compound is obtained by this method. These disulphurised monoalcohols are novel and form one of the subjects of the invention.

Stoichiometric trisulphurised monoalcohols of the formula R$^1$—S$_3$—CH$_2$—CH$_2$—OH, where R$^1$ represents a saturated or unsaturated monovalent aliphatic radical, may further be prepared either by reacting thiol R$^1$SH with methoxycarbonyldisulphanyl chloride CH$_3$—O—CO—S$_2$—Cl followed by a reaction between the product obtained and 2-mercaptoethanol, in the presence of a catalyst of the amine type such as N-methylmorpholine; or in the reverse order, by reacting 2-mercaptoethanol with methoxycarbonyldisulphanyl chloride followed by a reaction between the product obtained and thiol R$^1$—SH.

The (poly)sulphurised esters of the invention are obtained by condensing (poly)sulphurised alcohols as previously described with the appropriate carboxylic acids, under normal esterifying conditions.

The esterification catalyst may, for example, be para-toluenesulphonic acid.

When esterifying a polycarboxylic acid, one may consider esterifying it with a mixture of one or more (poly)sulphurised monoalcohols as described above and one or more conventional non-sulphurised monoalcohols, so as to vary the sulphur content of the mixture of esters. It is then advisable for at least one carboxylic function of the acid to be esterified by a (poly)sulphurised monoalcohol. The conventional monoalcohols used may e.g. be saturated aliphatic ones with 1 to 12 carbon atoms, i.e. from methanol to dodecanol.

The (poly)sulphurised compounds of the invention generally have a sulphur content of up to about 60% by weight. They have good anti-wear and extreme pressure properties and may advantageously be used as additives for inorganic or synthetic lubricating oils, particularly for gear lubricant oils and oils for metal work. The proportion of (poly)sulphurised compound in the oil may e.g. be from 0.05 to 20% by weight and more particularly from 0.2 to 5%.

As mentioned above, one of the advantages of the compounds according to the invention in their application as lubricant additives is the possibility of changing their anti-wear and extreme pressure properties by varying the number of sulphur atoms in the sulphurous chains (the value of the number x). Thus, given a constant concentration of sulphur in the lubricant, compounds with polysulphide chains prove to be more effective than monosulphide compounds, that is to say, compounds containing one (or more) isolated sulphur atoms. Hence the preferred compounds in the invention are those where the number x has a value strictly above 1 and more particularly a mean value of at least 2.

The following examples are given to illustrate the invention.

EXAMPLES

The preparation of sulphurised alcohols which will be used to prepare esters will be described first (Examples 1 to 7).

Example 1

Preparation of monosulphurised alcohol of the formula:

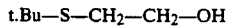

t.Bu—S—CH$_2$—CH$_2$—OH 10 g of caustic soda in pellet form (0.25 mol-g) is dissolved in 100 cm3 of ethyl alcohol. When it has dissolved, the mixture is brought to 50° C. then 22.5 g of 2-methyl-2 propanethiol (0.25 mol-g) is added. The temperature is kept at 50° C. for a further 0.5 hour after the addition is over.

14.33 g of chloroethanol (0.2 mol-g) is added drop by drop in the course of 1 hour with the temperature kept at 50° C., after which the mixture is brought to the reflux temperature of the solvent for 5 hours.

The mixture is cooled, 500 cm3 of water is added and the product concerned is extracted by agitating the previous mixture with 100 cm3 of dichloromethane. It is decanted and the organic phase recovered is washed with water, dried over anhydrous Na$_2$O$_4$, filtered then evaporated at 100° C. under reduced pressure.

23 g of a colourless viscous product is recovered, the elementary analysis of which is as follows:

| C % mass | | H % mass | | S % mass | |
|---|---|---|---|---|---|
| theory | found | theory | found | theory | found |
| 53.71 | 53.92 | 10.44 | 10.37 | 23.92 | 23.82 |

13C NMR and infra-red analysis confirm the structure of the product obtained.

Example 2

Preparation of bis (monosulphurised) alcohol of the formula:

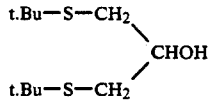

t.Bu—S—CH$_2$
　　　　　＼
　　　　　　CHOH
　　　　　／
t.Bu—S—CH$_2$

The experiment in Example 1 is repeated with the chloroethanol replaced by half the molar quantity (0.1 mole-g: 12.9 g) of 1,3-dichloropropanol. This reagent is introduced in the course of 1 hour at a reaction temperature from 25° to 30° C.

After the reaction then the treatment, 22 g of a colourless viscous product is recovered, the elementary analysis of which is as follows:

| C % mass | | H % mass | | S % mass | |
|---|---|---|---|---|---|
| theory | found | theory | found | theory | found |
| 55.90 | 55.95 | 10.16 | 10.25 | 27.16 | 27.32 |

13C NMR and infra-red analysis confirm the structure of the product obtained.

Example 3

Preparation of monosulphurised alcohol of the formula:

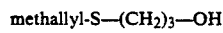

methallyl-S—(CH$_2$)$_3$—OH

At the first stage 2-methyl 1-propene 3-thiol is prepared by dissolving 41.9 g of thiourea (0.55 mol-g) in 80 cm3 of triethylene glycol brought to 75° C., then by gradually adding 45.25 g (0.5 mol-g) of methallyl chloride and keeping the reaction temperature below 130° C.

94.5 g of tetraethylene pentamine (0.5 mol-g) is thereupon added gradually. The thiol formed, which distills over (BP=40° C.), is collected and saved.

At the second stage 9.6 g (0.24 mol-g) of pure NAOH is dissolved in 200 cm3 of ethyl alcohol. When it has dissolved, 21.1 g (0.24 mol-g) of thiol prepared at the first stage is added gradually with the reaction temperature kept below 40° C. The mixture is brought to 50° C., kept at that temperature for 0.5 hour then cooled to 20° C.

18.9 g (0.2 mol-g) of 3-chloro 1-propanol is added gradually, then the mixture is brought to the reflux temperature, kept at that temperature for 6 hours, cooled and filtered to remove the NaCl formed.

The filtered alcohol solution is diluted with 1 000 cm3 of water, the sulphurous alcohol is extracted with benzene, and the organic solution recovered is dried over anhydrous Na$_2$SO$_4$, filtered and evaporated under reduced pressure. The sulphurous alcohol obtained (25 g) has the following analytical properties:

| C % mass | | H % mass | | S % mass | |
|---|---|---|---|---|---|
| theory | found | theory | found | theory | found |
| 57.67 | 57.51 | 9.62 | 9.58 | 21.88 | 21.95 |

Infra-red and 13C NMR analysis confirm the chemical structure of the product in question:

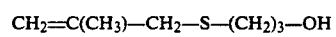

CH$_2$=C(CH$_3$)—CH$_2$—S—(CH$_2$)$_3$—OH

Example 4

Preparation of disulphurised alcohol of the formula:

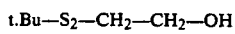
t.Bu—S$_2$—CH$_2$—CH$_2$—OH

This product is prepared by two different methods.

Method A

At the first stage 2-hydroxy-ethyl-methoxycarbonyl-disulphide CH$_3$—O—C(O)—S—S—CH$_2$—CH$_2$—OH is prepared by the synthesising method advocated by FIELD and RAVICHANDRAN (*J.Org.Chem.*, Vol.44 2624, 1979).

At the second stage 35 g of 2-hydroxy-ethyl-methoxycarbonyldisulphide (0.208 mol-g) is mixed with 50 cm3 of methanol and 1 cm3 of triethylamine. 18.72 g of 2-methyl-2-propane thiol (0.208 mol-g) is added in 1 hour at 25° C. When the methanol has evaporated at reduced pressure a liquid yellow product is recovered.

Method B

The experimental procedure in Example 1 is repeated, with 8 g of elemental sulphur (0.25 gram-atoms) added to the alcohol solution of sodium 2-methyl-2-propanethiolate, and with heating to 50° C. for an additional hour, to encourage the formation of statistical disulphide.

After the addition of chloroethanol then the treatments, a yellow liquid is recovered, with analytical properties similar to those of the non-statistical product obtained by Method A:

| Product of method | C % mass theory | C % mass found | H % mass theory | H % mass found | S % mass theory | S % mass found |
|---|---|---|---|---|---|---|
| A |  | 43.39 |  | 8.51 |  | 38.71 |
|   | 43.34 |  | 8.43 |  | 38.60 |  |
| B |  | 44.08 |  | 8.82 |  | 38.25 |

13C NMR analysis (which particularly shows the presence of S$_1$, S$_2$ and S$_3$ sulphides in the statistical product obtained by Method B) and infra-red analysis confirm the structure of the products obtained.

Example 5

Preparation of disulphurised alcohol of the formula:

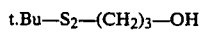
t.Bu—S$_2$—(CH$_2$)$_3$—OH

At the first stage 54 g (1.35 mol-g) of pure NAOH is dissolved in 2 500 cm3 of ethanol and 117 g (1.33 mol-g) of 2-methyl propane 2-thiol is gradually added with vigorous agitation. The mixture is heated to 50° C., then 42.6 g (1.33 gram-atom) of sulphur is added and the mixture is cooled to 20° C.

At the second stage 122.8 g (1.3 mol-g) of 3-chloro 1-propanol is gradually added to the previous mixture, then the mixture is brought to the reflux temperature. The rest of the experiment is carried out under the same conditions as in Example 1.

The crude polysulphurised alcohol recovered is purified by chromatography on silica gel; elution with hexane eliminates the alkyl polysulphides formed, and elution with methanol enables the required product to be obtained in solution.

After the methanol has evaporated under reduced pressure a yellow liquid is obtained, which has the following analytical properties:

| C % mass | | H % mass | | S % mass | |
|---|---|---|---|---|---|
| theory | found | theory | found | theory | found |
| 46.87 | 46.63 | 8.92 | 8.88 | 35.24 | 35.60 |

Infra-red analysis confirms the expected alcohol structure, and 13C NMR analysis shows there to be a mixture of sulphurised alcohols where the number of consecutive sulphur atoms is statistically equal to 2, as indicated in the following chemical formula (x=2):

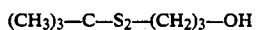
(CH$_3$)$_3$—C—S$_2$—(CH$_2$)$_3$—OH

Example 6

Preparation of a disulphurised alcohol of the formula:

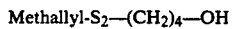
Methallyl-S$_2$—(CH$_2$)$_4$—OH

A hydroxyalkylthiosulphate is first prepared by dissolving 21.7 g of 4-chloro 1-butanol (0.2 mol-g) in 160 cm3 of methanol, adding 40 cm3 of water, bringing the mixture to the reflux temperature and adding 0.252 mol-g of sodium thiosulphate dissolved in 100 cm3 of water.

The mixture is kept boiling for 2 hours, then the methanol is evaporated off. When the mixture has cooled, the aqueous phase—previously washed with hexane—is saved.

17.6 g of 2-methyl 1-propene 3-thiol (0.2 mol-g) is then used. It is converted to sodium thiolate by the procedure in Example 3, but operating in an aqueous medium.

The two solutions are finally mixed at 0° C. and 100 cm3 of an aqueous solution saturated with NaCl is added. The temperature is allowed to return to 5° C. with agitation, and that temperature is maintained for an additional hour.

The organic component is then extracted with ethyl ether. When the organic phase has been washed with water, dried over anhydrous NA$_2$SO$_4$ and has evaporated under reduced pressure, 35 g of pale yellow liquid product is recovered.

| C % mass | | H % mass | | S % mass | |
|---|---|---|---|---|---|
| theory | found | theory | found | theory | found |
| 49.71 | 49.87 | 8.80 | 8.85 | 33.20 | 33.01 |

13C NMR analysis and infra-red analysis confirm the structure of the product obtained.

Example 7

Preparation of trisulphurised alcohol of the formula:

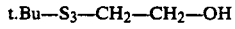
t.Bu—S$_3$—CH$_2$—CH$_2$—OH

At the first stage methoxycarbonyl tert-butyl trisulphide CH$_3$—O—C(O)—S$_3$-tert-butyl is prepared, using the synthesising method advocated by BARANY and MOTT (Syntheses communications 4, 657, 1984).

At the second stage 42.4 g of CH$_3$—O—C(O)—S$_3$-tert-butyl (0.2 mol-g) is dissolved in 500 cm3 of chloroform and 2 g of N-methylmorpholine and 15.6 g of mercaptoethanol are added. The mixture is agitated at 20° C. for 24 hours.

After treatment with 0.1N HCl, separation of the phases, drying of the organic phase and evaporation of the solvent under reduced pressure, 30 g of yellow viscous liquid is obtained.

| C % mass | | H % mass | | S % mass | |
|---|---|---|---|---|---|
| theory | found | theory | found | theory | found |
| 36.33 | 36.81 | 7.06 | 7.45 | 48.54 | 48.12 |

13C NMR and infra-red analysis confirm the structure of the product obtained.

Examples 8 to 15

Synthesis of esters

The method used is as follows. 21 mmol of sulphurised alcohol, 26 mmol of acid (propanoic or lauric), 40 mg of para-toluene sulphonic acid and 17 ml of cyclohexane are placed in a reactor equipped with a Dean Stark separator. The mixture is brought to reflux with agitation, and the treatment is continued until the required quantity of water is obtained. When the mixture has returned to room temperature, the organic phase is washed with a saturated solution of sodium bicarbonate, with water and with a saturated solution of sodium chloride. When the hexane has evaporated an oil of sufficient purity is separated (no trace of alcohol in NMR). In infra-red analysis all these products are characterised by a very strong band in the vicinity of 1740 cm$^{-1}$.

The sulphurised alcohols and acids used are as follows:

| Example | Carboxylic acid | Sulphurised alcohol of Example |
|---|---|---|
| 8 | Dodecanoic acid | 1 |
| 9 | Propanoic acid | 1 |
| 10 | Propanoic acid | 2 |
| 11 | Dodecanoic acid | 2 |
| 12 | Dodecanoic acid | 3 |
| 13 | Dodecanoic acid | 4B |
| 14 | Propanoic acid | 5 |
| 15 | Dodecanoic acid | 6A |

The analytical characteristics of these products are set out in Table 1 below.

TABLE 1

| | Characteristics of esters obtained | | | | | |
|---|---|---|---|---|---|---|
| | C % mass | | H % mass | | S % mass | |
| Example | theory | found | theory | found | theory | found |
| 8 | 68.34 | 68.84 | 11.39 | 11.88 | 10.14 | 9.78 |
| 9 | 56.82 | 57.34 | 9.47 | 9.69 | 16.87 | 16.11 |

TABLE 1-continued

| | Characteristics of esters obtained | | | | | |
|---|---|---|---|---|---|---|
| | C % mass | | H % mass | | S % mass | |
| Example | theory | found | theory | found | theory | found |
| 10 | 57.51 | 58.21 | 9.58 | 10.25 | 21.95 | 21.12 |
| 11 | 66.01 | 66.67 | 11.00 | 11.57 | 15.37 | 14.87 |
| 12 | 69.50 | 69.97 | 10.97 | 11.25 | 9.77 | 9.65 |
| 13 | 62.05 | 62.67 | 10.34 | 10.65 | 18.42 | 18.11 |
| 14 | 50.82 | 51.33 | 8.47 | 8.87 | 27.16 | 26.67 |
| 15 | 64.15 | 64.76 | 10.16 | 10.41 | 17.14 | 17.00 |

Example 16

Assessment of the extreme pressure and anti-wear properties of the additives according to the invention Tests are carried out to show the extreme pressure and anti-wear properties of the esters in Examples 8 and 12 to 15, using a 4 ball machine in accordance with the procedure in ASTM D 2783, at concentrations such that the sulphur content provided by the additive in mineral oil SAE 80W90 equals 0.22% by mass. The results obtained are set out in Table 2.

It will be seen from the results that the additives of the invention have good anti-wear and extreme pressure properties, and that these can be changed according to the quantity of elemental sulphur used in the synthesis.

It will be appreciated in particular that, given a constant concentration of sulphur in the basic oil, esters with polysulphide structures are more effective in reducing wear than those with monosulphide structures, and that for a given mono or polysulphide structure ethylene esters are more effective than saturated ones, particularly when the unsaturation is in position β relative to the C—S bond (C=C—C—S~). Hence it is possible to control the mechanical performance of these products at will.

This improvement can be exploited in formulating lubricating oils for gears or for metal work.

TABLE 2

| | | | | FOUR BALL MACHINE | | | | | | |
|---|---|---|---|---|---|---|---|---|---|---|
| | Concentration of S in additive | Concentration of additive in oil | Concentration of S due to additive in | EXTREME PRESSURE | | | | WEAR Diameter of impression (mm) | | |
| | | | | Load-wear index | | Welding load | | 40 kgf | 60 kgf | 80 kgf |
| Ester of example | % mass | % mass | oil % mass | kgf | N | kgf | N | 392,4 N | 588,6 N | 784,8 N |
| oil alone | — | 0 | — | 22,50 | 220,7 | 160 | 1569,5 | 0,82 | 1,98 | 2,08 |
| 8 | 9,78 | 2,25 | 0,22 | 32,75 | 321,3 | 200 | 1962,0 | 0,39 | 0,56 | 1,10 |
| 13 | 18,11 | 1,21 | 0,22 | 45,1 | 442,4 | 200 | 1962,0 | 0,34 | 0,49 | 0,83 |
| 14 | 26,67 | 0,83 | 0,22 | 42,2 | 414,0 | 200 | 1962,0 | 0,33 | 0,53 | 0,91 |
| 12 | 9,65 | 2,28 | 0,22 | 40,5 | 397,3 | 200 | 1962,0 | 0,38 | 0,56 | 1,00 |
| 15 | 17,00 | 1,29 | 0,22 | 49,8 | 488,5 | 250 | 2452,5 | 0,32 | 0,51 | 0,78 |

We claim:

1. A carboxylic compound of the formula

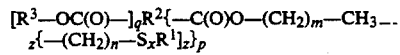

$[R^3—OC(O)—]_qR^2\{—C(O)O—(CH_2)_m—CH_3—_z\{—(CH_2)_n—S_xR^1]_z\}_p$ wherein
$R^1$ represents a saturated or unsaturated monovalent aliphatic radical with 1 to 30 carbon atoms;
x is a number greater than 1;
z equals 1 or 2; when z equals 1, n is an integer from 0 to 5, m is an integer from 0 to 5, and m+n is an integer from 1 to 10; when z equals 2, n is an integer from 1 to 5, m is an integer from 0 to 5, and m+n is an integer from 1 t 10;

$R^2$ is a hydrocarbon radical with 1 to 51 carbon atoms and a valency of p+q;

$R^3$ is a hydrogen atom or a monovalent aliphatic radical with 1 to 30 carbon atoms;

p is an integer from 1 to 4; and q is an integer from 0 to 3, with p+q being an integer from 1 to 4.

2. A compound of claim 1, wherein q equals zero.

3. A compound of claim 2, wherein p equals 1 and $R^2$ is a monovalent aliphatic radical with 1 to 21 carbon atoms.

4. A compound of claim 1, wherein z equals 1, m equals zero, $R^1$ represents a monovalent aliphatic radical with 1 to 12 carbon atoms and x has a value of approximately 1 to 3.

5. A compound of claim 2, wherein z equals 1, m equals zero, $R^1$ represents a monovalent aliphatic radical with 1 to 12 carbon atoms and x has a value of approximately 1 to 3.

6. A compound of claim 5, wherein x has a mean value of at least 2.

7. A compound of claim 1, wherein $R^1$ is a saturated or unsaturated monovalent aliphatic radical with 1-12 carbon atoms.

8. A compound of claim 1, wherein the sulfur content of said compound is up to 60% by weight.

9. A compound according to claim 1, wherein x is 2.

10. A compound according to claim 1, wherein x is 3.

11. A compound according to claim 1, wherein n is 1-5.

12. A lubricating composition, comprising:
mineral or synthetic lubricating oil; and
at least one carboxylic compound according to claim 1, in an amount sufficient to improve anti-wear and extreme pressure properties.

13. A lubricating composition of claim 12, wherein said amount is 0.05 to 20% by weight.

14. A composition according to claim 13, wherein said amount is 0.2-5% by weight.

15. A composition comprising two or more compounds of the formula

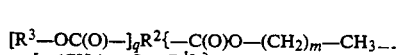

wherein $R^1$ represents a saturated or unsaturated monovalent aliphatic radical with 1 to 30 carbon atoms;

x is a number equal to or greater than 1;

z equals 1 or 2; when z equals 1, n is an integer from 0 to 5, m is an integer from 0 to 5, and m+n is an integer from 1 to 10; when z equals 2, n is an integer from 1 to 5, m is an integer from 0 to 5, and m+n is an integer from 1 t 10;

$R^2$ is a hydrocarbon radical with 1 to 51 carbon atoms and a valency of p+q;

$R^3$ is a hydrogen atom or a monovalent aliphatic radical with 1 to 30 carbon atoms;

p is an integer from 1 to 4; and q is an integer from 0 to 3, with p+q being an integer from 1 to 4; and wherein the overall mean value of x is greater than 1.

16. A lubricating composition, comprising:
mineral or synthetic lubricating oil; and
a composition according to claim 15, in an amount sufficient to improve anti-wear and extreme pressure properties.

17. A carboxylic compound of the formula

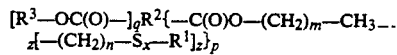

wherein $R^1$ is a monovalent saturated aliphatic radical with 1-30 carbon atoms;

x is a number equal to or greater than 1;

z equals 1 or 2; when z equals 1, n is an integer from 0 to 5, m is an integer from 0 to 5, and m+n is an integer from 1 to 10; when z equals 2, n is an integer from 1 to 5, m is an integer from 0 to 5, and m+n is an integer from 1 t 10;

$R^2$ is a saturated aliphatic radical having 1-51 carbon atoms and a valency of p+q;

$R^3$ is a hydrogen atom or a monovalent aliphatic radical with 1 to 30 carbon atoms;

p is an integer from 1 to 4; and q is an integer from 0 to 3, with p+q being an integer from 1 to 4.

18. A compound according to claim 17, wherein $R^1$ is a monovalent saturated aliphatic radical having 1-12 carbon atoms.

19. A compound according to claim 18, wherein $R^1$ is tert-butyl.

20. A lubricating composition comprising:
mineral or synthetic lubricating oil, and
at least one carboxylic acid compound according to the formula

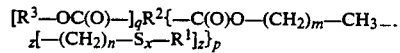

wherein $R^1$ represents a saturated or unsaturated monovalent aliphatic radical with 1 to 30 carbon atoms;

x is a number equal to or greater than 1;

z equals 1 or 2; when z equals 1, n is an integer from 0 to 5, m is an integer from 0 to 5, and m+n is an integer from 1 to 10; when z equals 2, n is an integer from 1 to 5, m is an integer from 0 to 5, and m+n is an integer from 1 t 10;

$R^2$ is a saturated aliphatic radical having 1-51 carbon atoms and a valency of p+q;

$R^3$ is a hydrogen atom or a monovalent aliphatic radical with 1 to 30 carbon atoms;

p is an integer from 1 to 4; and q is an integer from 0 to 3, with p+q being an integer from 1 to 4, wherein the amount of said carboxylic compound is sufficient to improve anti-wear and extreme pressure properties.

21. A composition according to claim 20, wherein $R^1$ is a saturated or unsaturated monovalent aliphatic radical having 1-12 carbon atoms.

22. A composition according to claim 21, wherein $R^1$ is tert-butyl or methallyl.

* * * * *